United States Patent
Dees

(10) Patent No.: US 7,201,914 B2
(45) Date of Patent: Apr. 10, 2007

(54) COMBINATION ANTIPERSPIRANT AND ANTIMICROBIAL COMPOSITION

(75) Inventor: H. Craig Dees, Knoxville, TN (US)

(73) Assignee: Xantech Pharmaceuticals, Inc., Knoxville, TN (US)

( * ) Notice: Subject to any disclaimer, the term of this patent is extended or adjusted under 35 U.S.C. 154(b) by 382 days.

(21) Appl. No.: 10/425,255

(22) Filed: Apr. 29, 2003

(65) Prior Publication Data

US 2003/0215408 A1   Nov. 20, 2003

Related U.S. Application Data

(60) Provisional application No. 60/381,363, filed on May 17, 2002.

(51) Int. Cl.
*A61K 8/02* (2006.01)
*A61Q 15/00* (2006.01)
*A01N 25/00* (2006.01)

(52) U.S. Cl. .............. 424/401; 424/65; 424/68; 424/400; 424/404; 514/859

(58) Field of Classification Search ........... 424/65, 424/68, 400, 401, 404; 514/859
See application file for complete search history.

(56) References Cited

U.S. PATENT DOCUMENTS

| | | | |
|---|---|---|---|
| 5,288,480 A | 2/1994 | Gaffar et al. | |
| 5,344,641 A | 9/1994 | Gaffar et al. | |
| 5,624,666 A | 4/1997 | Coffindaffer et al. | .... 424/70.21 |
| 6,046,238 A * | 4/2000 | Yu et al. | ..................... 514/553 |
| 6,099,827 A | 8/2000 | Esser | ........................... 424/65 |
| 6,221,345 B1 | 4/2001 | Esser | ........................... 424/65 |
| 6,384,023 B2 | 5/2002 | Singleton et al. | ........... 514/159 |
| 6,387,357 B1 | 5/2002 | Chopra et al. | |
| 6,426,061 B1 * | 7/2002 | Li et al. | ....................... 424/65 |

FOREIGN PATENT DOCUMENTS

| | | |
|---|---|---|
| EP | 1 080 715 A2 | 3/2001 |
| EP | 1 181 866 A1 | 2/2002 |
| GB | 2 274 989 A | 8/1994 |
| WO | WO 94/12115 | 6/1994 |

OTHER PUBLICATIONS

European Search Report dated Sep. 21, 2004 for European Application No. 03253063.6.

* cited by examiner

*Primary Examiner*—Shelley A. Dodson
(74) *Attorney, Agent, or Firm*—Cook, Alex, McFarron, Manzo, Cummings & Mehler, Ltd.

(57) ABSTRACT

New medicaments and compositions having an antiperspirant agent and an antimicrobial agent, and methods based thereof, for control, prevention, amelioration, or treatment of perspiration and topical microbial contamination or infection of skin of the hands, feet, groin, face and other areas of the body, along with reduction or control of symptoms and side effects of such perspiration and microbial contamination or infection, are disclosed. Such medicaments and compositions can be used for various cosmetic, medicinal or pharmaceutical purposes, including control of microbial growth on gloved hands, control of microbial contamination of hands, control of chronic irritation or infection of hands, feet, groin, head, or other areas of skin associated with athletic participation, control of facial acne or other similar conditions, as a cosmetic foundation, or for control of foot odor or excessive foot perspiration.

27 Claims, No Drawings

COMBINATION ANTIPERSPIRANT AND ANTIMICROBIAL COMPOSITION

This application claims the benefit of provisional application U.S. Ser. No. 60/381,363 filed May 17, 2002.

BACKGROUND OF THE INVENTION

The present invention is directed to medicaments, compositions and methods for control, prevention, amelioration, or treatment of perspiration and topical microbial contamination or infection of skin of the hands, feet, groin, face and other areas of the body, along with reduction or control of symptoms and side effects of such perspiration and microbial contamination or infection. Such medicaments and compositions can be used in various cosmetic, medicinal and pharmaceutical products. Such medicaments also have application for athletic activities.

A range of dermatologic maladies, including inflammation, pruritus, chapping, chaffing, irritation, folliculitis, impetigo, acne, tinea, candidiasis, atopic dermatitis, contact dermatitis, eczema (acute, subacute and chronic), and seborrhea of the skin may, in many instances, be caused by a diagnosed or undiagnosed superficial infection with one or more microbes, including various bacteria, fungi and protozoa. Such microbes may be spread to other skin areas or to other individuals unless adequately controlled, and can proliferate as a result of common occupational or personal activities. Moreover, the symptoms caused by such infection may be chronic and highly resistant to conventional treatments, some of which may serve only to exacerbate the problem.

For example, increasing occupational usage of close-fitting, non-porous gloves ("protective gloves") for prolonged periods of time (for example, by healthcare professionals, emergency response personnel, laboratory workers, security personnel, mail handlers, etc.) has been associated with a commensurate increase in localized maladies of the hands of these wearers. Moreover, prolonged usage can result in compliance problems due to perspiration of the hands that leads to glove slippage, loss of dexterity, and incomplete usage. Several examples serve to illustrate recent trends:

Concerns over possible exposure to the Human Immunodeficiency Virus (HIV) has led to establishment of strict procedures meant to protect individuals from infection with HIV, which is commonly believed to be the cause of Acquired Immune Deficiency Syndrome (AIDS). Protective gloves are now worn by medical personnel that formerly did not wear gloves (e.g., orderlies, nurses, laboratory personnel and paramedics), and these gloves are being worn for much longer periods of time than in the past. Physicians and dentists are also now required to wear protective gloves to prevent transmission of HIV. Firefighters, police and others that might come in contact with infected individuals or biological fluids are also wearing protective gloves.

Other professionals have commonly worn protective gloves during the practice of their profession prior to the onset of the AIDS crisis. Laboratory researchers and associated personnel wear gloves similar to those used by healthcare providers for prolonged periods to prevent contamination of hands by hazardous materials and to prevent samples from being contaminated with biological or other materials present on the hands.

Recent efforts aimed at heightening security have also markedly increased the use of protective gloves. For example, increased security due to possible terrorist threats have caused airlines to increase searches of passengers and their luggage. Most of the security personal conducting security searches of passengers and baggage wear disposable protective gloves. Related concern over anthrax spores sent through the U.S. postal system has led to widespread use of protective gloves by mail sorters and other Postal Service personnel.

The remarkable increase in use of disposable protective glove use is exemplified by the following statistics: in 1990, over 550 million pairs of gloves were sold in the U.S.; this number increased to an estimated 1.8 billion pairs by 1994, comprising a greater than 20% per annum growth rate. A recent estimate of the U.S. medical market for disposable gloves exceeds $1.2 billion annually. Thus, any health or compliance problems associated with protective glove use are likely to mount at a rate commensurate with the increasing number of gloves sold.

Both compliance and adverse health effects associated with long-term use of close-fitting, non-porous protective gloves appear to result from the very features intended to prevent exposure to or transfer of hazardous or undesirable agents. First, the close fit and non-porosity of the gloves increases perspiration of the hands and keeps this perspiration within the gloves. The resultant moisture within the gloves makes the gloves uncomfortable and may cause them to slip off or shift around on the hand. Slipping or shifting of gloves due to perspiration can make the manipulation of objects and the performance of complex tasks difficult. Loss of a glove or slippage of the sleeve down the hand or wrist can result in exposure of the wearer to the agents which the glove is supposed to resist; similarly, the resultant exposed skin, along with perspiration leaking from the gloves, can contaminate materials that are to be protected from exposure to human flora or secretions. Second, long-term glove usage can irritate the skin or provoke allergic reactions on the hands. Perspiration inside the gloves may exacerbate this problem. Third, increased levels of moisture on the hands may increase bacterial levels found on the hands. These bacteria can arise from normal flora of the hands themselves or from powders (e.g., cornstarch, talc) or other materials inside the gloves themselves that may contain a high number of bacteria. These proliferating bacteria can cause irritation or allergic reactions or otherwise infect the glove wearer.

Thus, prior art in protective gloves cannot cope with long-term use of gloves that chronically subjects wearers' hands to a moist, unsterile local environment. Current sales trends reflect increased use of gloves to prevent contamination with hazardous agents and widespread use by new sectors of the workforce. Nonetheless, problems related to hand perspiration and microbial proliferation in such gloves may lead to significant operator non-compliance (i.e., not wearing the gloves), potentially exposing the operator, employer, or customer to undesirable consequences (such as exposure to a serious disease like AIDS or Hepatitis B).

Furthermore, current glove technologies do not afford protection against microbial contamination (including contamination with viruses) should glove integrity be compromised. For example, if there is even a minute hole in the glove, no mechanism is available to combat microbes that might get through the barrier, thereby possibly exposing the wearer to a fatal or chronic disease.

Other undesirable skin maladies are also associated with conditions that promote or allow unchecked growth of bacteria on or within perspiring skin. For example, acne occurs when increased production of skin lipids causes the pores of the skin to close or be blocked. This causes further skin secretions (primarily perspiration and lipids) to back up within the pores. Normal flora can then proliferate in such pores, fueled by the body's own secretions of moisture (perspiration) and fuel (lipids). The body responds to this mounting bacterial load and build up of skin secretions with an inflammatory reaction, producing the hallmark acne lesions.

Current approaches to acne treatment can be highly undesirable. Analogs of normal body lipids (e.g., cis-retin A, retinol) are often used to disrupt production of skin lipids. However, cis-retin A is a powerful teratogen capable of inducing developmental abnormalities in a developing fetus or nursing infant of female patients, and may also be associated with psychotic behavior and suicide, particularly in teenage patients. In contrast, non-prescription agents (e.g., over-the-counter products, also known by the acronym OTC) approved for acne are generally ineffective. For example, a 2% solution of salicylic acid provides only a slight reduction in skin oils. Preparations based on coal tar also reduce skin oils, but are potent carcinogens when applied topically.

Other skin conditions are also produced or exacerbated by the combination of microbial infection, chronic moisture and the host's response, including tinea pedis (athlete's foot), tinea cruris (jock itch), psoriasis, seborrhea and eczema.

Thus, an effective method to simultaneously prevent proliferation of microbes and undesirable responses of the host (e.g, increased production of perspiration, lipids, or inflammatory response) without severe adverse consequences or risks is required. A product that also decreases the discomfort associated with frequent or prolonged use of disposable gloves is needed to prevent or alleviate such problems and to increase user compliance.

While there have been prior descriptions of possible uses of various antiperspirant or antimicrobial agents, it is not believed that such agents have been used or described in combination for control of skin pathogens. For example, Singleton et al. (U.S. Pat. No. 6,384,023), describes certain topical compositions for prevention and treatment of acne or seborrhea that include antimicrobial agents. Coffindaffer et al. (U.S. Pat. No. 5,624,666), describes certain topical compositions for prevention and treatment of dandruff that also include antimicrobial agents. Esser (U.S. Pat. No. 6,099,827 and U.S. Pat. No. 6,221,345), describe certain topical compositions for application as an antiperspirant. Each of these references only uses one or the other of these agents, not both. Further, no glove powder or topical hand-care composition is known to Applicants to contain both antiperspirant and antimicrobial active ingredients.

Accordingly, it is an object of the present invention to overcome these prior failures and to provide methods and compositions based on such methods that control, prevent, ameliorate, or otherwise treat undesirable perspiration and topical microbial contamination or infection of skin of the hands, feet, groin, face and other areas of the body, and reduce or control of symptoms and side effects of such perspiration and microbial contamination or infection.

SUMMARY OF THE INVENTION

The present invention is directed to medicaments, compositions and methods comprising an antiperspirant agent and an antimicrobial agent to control, prevent, ameliorate, or otherwise treat undesirable perspiration and topical microbial contamination or infection of skin of the hands, feet, groin, face and other areas of the body, and reduce or control symptoms and side effects of such perspiration and microbial contamination or infection.

One embodiment of the present invention comprises a combination of a topical antiperspirant and a topical antimicrobial agent, wherein the effects of such combination are superior to the use of either active component alone.

The present invention is also directed to cosmetics, medicaments, and pharmaceutical compositions and agents comprising a combination of an antiperspirant agent and an antimicrobial agent for control of microbial growth on gloved hands, control of microbial contamination of hands, control of chronic irritation or infection of hands, feet, groin, head, and other areas of skin associated with athletic participation, control of facial acne and other conditions, as a cosmetic foundation, and for control of foot odor and excessive foot perspiration. In a preferred embodiment, each of the cosmetics, medicaments, and pharmaceutical compositions and agents is a topical agent.

In a further embodiment of the present invention, an antiviral agent, a bacteriocide agent, a bacteriostat agent, a moister sealant or an anti-inflammatory agent can be included in the medicament or composition of the present invention.

DETAILED DESCRIPTION OF THE PRESENTLY PREFERRED EMBODIMENTS

The present invention comprises methods and compositions based on such methods that control, prevent, ameliorate, or otherwise treat undesirable perspiration and topical microbial contamination or infection of skin of the hands, feet, groin, face and other areas of the body, and reduce or control symptoms and side effects of such perspiration and microbial contamination or infection. A key feature of the present invention is a combination of a topical antiperspirant and a topical antimicrobial agent, wherein the effects of such combination are superior to the use of either active component alone. The term antiperspirant is defined herein as those agents that check, reduce or eliminate perspiration. Examples include aluminum glycinate, aluminum chlorohydrate glycinate, or zinc chlorohydrate; additional examples of antiperspirant agents are listed in Table 1. The term antimicrobial is defined herein as those agents that are biocidal or biostatic (e.g., destroy or inhibit the growth of one or more microorganisms, including bacteria, fungi, protozoa, and viruses). Some examples of antimicrobial agents are listed in Table 2.

TABLE 1

Example antiperspirant agents (i.e., active ingredients) and preferred ranges of concentration.

| Active Ingredient | Concentration |
| --- | --- |
| Aluminum chlorohydrate (1.9:1 to 2.1:1 Al:Cl ratio) | 25% or less (1) |
| 'Activated' aluminum chlorohydrate (AACH) | 25% or less (1) |
| Aluminum chlorohydrate glycine complex | 25% or less (1) |
| Aluminum dichlorohydrate (0.9:1 to 1.25:1 Al:Cl ratio) | 25% or less (1) |
| Aluminum sesquichlorohydrate (1.25:1 to 1.9:1 Al:Cl ratio) | 25% or less (1) |
| Aluminum zirconium trichlorohydrate (1.5:1 to 2.1:1 Al:Cl ratio; 2.0:1 to 6.0:1 Al:Zr ratio) | 20% or less (1) |
| Aluminum zirconium tetrachlorohydrate (0.9:1 to 1.5:1 Al:Cl ratio; 2.0:1 to 6.0:1 Al:Zr ratio) | 20% or less (1) |
| Aluminum zirconium pentachlorohydrate (1.5:1 to 2.1:1 Al:Cl ratio; 6.0:1 to 10.0:1 Al:Zr ratio) | 20% or less (1) |
| Aluminum zirconium octachlorohydrate (0.9:1 to 1.5:1 Al:Cl ratio; 2.0:1 to 10.0:1 Al:Zr ratio) | 20% or less (1) |
| Aluminum zirconium trichlorohydrex glycine complex (1.5:1 to 2.1:1 Al:Cl ratio; 2.0:1 to 6.0:1 Al:Zr ratio) | 20% or less (1) |

TABLE 1-continued

Example antiperspirant agents (i.e., active ingredients) and preferred ranges of concentration.

| Active Ingredient | Concentration |
|---|---|
| Aluminum zirconium tetrachlorohydrex glycine complex (0.9:1 to 1.5:1 Al:Cl ratio; 2.0:1 to 6.0:1 Al:Zr ratio) | 20% or less (1) |
| Aluminum zirconium pentachlorohydrex glycine complex (1.5:1 to 2.1:1 Al:Cl ratio; 6.0:1 to 10.0:1 Al:Zr ratio) | 20% or less (1) |
| Aluminum zirconium octachlorohydrex glycine complex (0.9:1 to 1.5:1 Al:Cl ratio; 6.0:1 to 10.0:1 Al:Zr ratio) | 20% or less (1) |
| Sodium aluminum chlorhydroxy lactate | 25% or less (1) |
| Aluminum zirconium tetrachlorohydrate | 25% or less (1) |
| Aluminum chlorohydrex PG complex (0.9:1 to 1.25:1 Al:Cl ratio) | 25% or less (1) |
| Aluminum dichlorohydrex PG complex (1.25:1 to 1.9:1 Al:Cl ratio) | 25% or less (1) |
| Aluminum sesquichlorohydrex PG complex (1.25:1 to 1.9:1 Al:Cl ratio) | 25% or less (1) |
| Aluminum chlorohydrex PEG complex (1.9:1 to 2.1:1 Al:Cl ratio) | 25% or less (1) |
| Aluminum dichlorohydrex PEG complex (0.9:1 to 1.25:1 Al:Cl ratio) | 25% or less (1) |
| Aluminum sesquichlorohydrex PEG complex (1.25:1 to 1.9:1 Al:Cl ratio) | 25% or less (1) |
| 'Activated' Aluminum zirconium tetrachlorohydrex gly (AZAG) | 25% or less (1) |
| Aluminum glycinate | 25% or less (1) |
| Zinc chlorohydrate | 10% or less (1) |
| Aluminum chloride | 15% or less (2) |
| Aluminum sulfate | 10% or less (3) |

(1) Percentage on an anhydrous basis (omitting any buffer component)
(2) Percentage based on the hexahydrate form
(3) Concentration of aluminum sulfate buffered with equal concentration of sodium aluminum lactate

TABLE 2

Example antimicrobial agents (i.e., active ingredients) and preferred ranges of concentration.

| Active Ingredient | Concentration |
|---|---|
| Alkydimethylbenzalkonium chloride | 5% or less |
| Benzalkonium chloride | 5% or less |
| Benzethonium chloride | 5% or less |
| Benzyl alcohol | 4% or less |
| Butylparaben | 0.2% or less |
| Chlorhexidine | 5% or less |
| Chlorobutanol | 0.5% or less |
| Chloroxylenol | 5% or less |
| Chloflucarban | 5% or less |
| Cloquinol | 5% or less |
| Cocamidopropyl PG-dimonium chloride phosphate | 5% or less |
| Ethyl alcohol | 50–95% |
| Farnesol | 1% or less |
| Fluorosalan | 5% or less |
| Hexachlorophene | 0.1% or less |
| Hexylresorcinol | 5% or less |
| Imidurea | 0.5% or less |
| Iodine complex | 10% or less |
| Isopropyl alcohol | 50–90% |
| Mercufenol chloride | 10% or less |
| Methylbenzethonium chloride | 5% or less |
| Methylparaben | 0.3% or less |
| Metronidazole | 1% or less |
| Nonylphenoxypoly (ethyleneoxy) ethanoliodine | 10% or less |
| Octoxy glycerine | 2% or less |
| Phenol | 10% or less |
| Poloxamer-iodine complex | 10% or less |
| Polyhexamethylene buguanide (PHMB) | 5% or less |
| Propylparaben | 0.2% or less |
| Providone iondine | 10% or less |
| Quaternary ammonium compounds (QACs) | 5% or less |
| Secondary amyltricresols | 10% or less |

TABLE 2-continued

Example antimicrobial agents (i.e., active ingredients) and preferred ranges of concentration.

| Active Ingredient | Concentration |
|---|---|
| Sodium benzoate | 0.1% or less |
| Sodium oxychlorosene | 10% or less |
| Tribromsalan | 2% or less |
| Triclocarban | 2% or less |
| Triclosan | 2% or less |
| Undecoylium chloride iodine complex | 10% or less |
| Usnic acid | 0.1% or less |
| Zinc phenosulfonate | 5% or less |

The following examples of the present invention will serve to illustrate some of the benefits of the present invention.

EXAMPLE 1

Control of Microbial Growth on Gloved Hands

In this example, hands were pre-treated with either (1) a bacteriostat or antimicrobial lotion, ca. 2% benzalkonium chloride; (2) an antiperspirant lotion, ca. 7% zinc chlorohydrate in an oil-in-water emulsion; or (3) a combination antiperspirant and bacteriostat composition, ca. 7% zinc chlorohydrate and ca. 2% benzalkonium chloride, prior to placement of gloves on the hands. The gloves were then kept on for 6 hours of continuous use. After 6 hours, the hands were tested for microbial levels. As a control, an untreated hand was tested before glove use and untreated hands were placed into gloves, which were used for 6 hours, then the hands were tested.

A comparison of microbial levels on the skin following prolonged glove use (see Table 3) illustrates that the combination of the lotion with the antiperspirant and the bacteriostat composition is superior to the effects obtained by using either active ingredient alone. These data show that the number of bacteria isolated from the skin after 6 hours of continuous glove use increased markedly (e.g., there is a statistically significant elevation of colony forming units, CFUs, following glove use relative to no-glove controls). Application of either an antiperspirant lotion (e.g., ca. 7% zinc chlorohydrate in an oil-in-water emulsion) or antimicrobial lotion (e.g., ca. 2% benzalkonium chloride) alone to the hands prior to glove use produced a statistically significant reduction in the number of bacteria after 6 hours (relative to untreated glove use alone), but any differences in such reduction are not statistically significant when comparing the effects of either lotion alone. In contrast, application of a combined lotion composition, containing both antiperspirant and antimicrobial ingredients (e.g., ca. 7% zinc chlorohydrate and ca. 2% benzalkonium chloride), to the hands prior to glove use produced a marked reduction in the number of bacteria after 6 hours that is statistically significant relative to all other test groups.

A second test was done using powder compositions applied to hands prior to glove use. In this test, hands were pretreated with either (1) a bacteriostat or antimicrobial powder, ca. 2% benzalkonium chloride; (2) an antiperspirant powder, talc containing ca. 7% zinc chlorohydrate; or (3) a powder composition with both antiperspirant and antimicrobial ingredients, 7% zinc chlorohydrate and ca. 2% benzalkonium chloride, prior to glove use. The gloves were then kept on for 6 hours of continuous use, and the hands were then tested for microbial levels. The same type of control as used above was also used for this test.

The use of a powder composition in this test had a similar outcome to the lotion composition in the test above. Application of either an antiperspirant powder (e.g., talc containing ca. 7% zinc chlorohydrate) or antimicrobial powder (e.g., ca. 2% benzalkonium chloride) to gloves prior to use produces a statistically significant reduction in the number of bacteria after 6 hours (relative to untreated glove use alone), but any differences in such reduction are not statistically significant when comparing the effects of either powder alone. In contrast, application of a combined powder composition, containing both antiperspirant and antimicrobial ingredients (e.g., ca. 7% zinc chlorohydrate and ca. 2% benzalkonium chloride), to the gloves prior to use produced a marked reduction in the number of bacteria after 6 hours that is statistically significant relative to all other test groups.

TABLE 3

Synergistic effect of combined antiperspirant and antimicrobial compositions.
Comparison of colony forming units (CFUs) per 50 mL of glove rinsate (tryptocase soy broth). Broth was poured onto hands or into gloves as indicated, collected, filtered through 0.22 µm filter, then cultured on same filter. Data represent mean CFUs for triplicate trials, analyzed via two-way ANOVA and Student's t-test to correct for multiple means and pooled variance.

| Treatment Group | Type 1 - Lotion | Type 2 - Powder |
| --- | --- | --- |
| Control (untreated hand before glove use) | 50.5 ± 6.3 | 31.2 ± 4.5 |
| Untreated hand after 6 hours in glove | 77.0 ± 13.0 | 65.4 ± 8.7 |
| Hand pre-treated with bacteriostat only (after 6 hours in glove) | 24.0 ± 6.0 | 25.8 ± 4.2 |
| Hand pre-treated with antiperspirant only (after 6 hours in glove) | 29.2 ± 9.4 | 27.8 ± 5.4 |
| Hand pre-treated with antiperspirant and bacteriostat composition (after 6 hours in glove) | 5.2 ± 8.2 | 2.8 ± 4.4 |

Thus, use of a glove powder or topical handcare composition containing a combination of antiperspirant and antimicrobial ingredients prior to glove use produces a statistically significant reduction in number of bacteria that is superior to that achieved by use of an antiperspirant or antimicrobial composition alone. This demonstrates that it is possible to control proliferation of microbes emanating from within gloves through use of a combined antiperspirant and antimicrobial composition.

Example 2

Control of Facial Acne and Other Conditions

In this example, a bacteria commonly associated with acne (e.g., *Propionibaclerium acnes*) was studied. *P. acnes* is an anaerobic bacterium that can be cultured in anaerobic media. In this test, inoculation of anaerobic growth media (thioglycollate broth was used in this example) with *P. acnes*, followed by incubation overnight, yielded a turbid culture containing $10^4$–$10^6$ bacteria per cubic centimeter. Introduction of a combined antiperspirant and antimicrobial composition of the present invention (i.e., a lotion containing 16% Aluminum zirconium trichlorohydrex glycine complex and 0.2% benzethonium chloride) to the media (1:200 dilution of the composition in media), followed by similar inoculation and incubation, yielded no observable growth of *P. acnes*. Thus, use of the composition suppresses growth of *P. acnes*. Hence, the combined antiperspirant and antimicrobial composition prevents the growth of bacteria commonly associated with acne.

In addition to this in vitro evidence, the topical application of such a composition to skin exhibiting mild- to moderate-grade acne was found to significantly reduce the appearance of such mild- to moderate-grade acne within several days following application. Such reduction appears to occur due to the combined effects of the antiperspirant (which may reduce available skin moisture, thus reducing conditions favorable to bacterial growth) and antimicrobial (which destroy or inhibit the growth of bacteria) agents.

Moreover, in addition to these apparent antimicrobial effects, use of such compositions appears to reduce excess sebum production, and may thereby improve the overall appearance of skin afflicted with acne, as well as that of other skin exhibiting symptoms of excess sebum production, including that associated with seborrhea. Such excess sebum production may be associated with low-grade irritation caused by the presence of certain chronic dermatophytes, and use of such compositions is believed to control proliferation of such dermatophytes in a manner similar to that involved in control of acne.

The compositions of the present invention have a number of additional applications, as illustrated in the following examples.

Example 3

Control of Microbial Contamination of Hands

The combined antiperspirant and antimicrobial composition of the present invention can prevent infection or serious contamination of gloved hands with exogenous microbes should glove integrity be compromised, for example through tearing or puncturing.

For example, currently produced protective gloves have no provision for inhibiting or destroying viruses (e.g., such as HIV or Hepatitis B) or bacteria that might contaminate a gloved hand upon loss of glove integrity. A glove powder or topical handcare composition of the present invention that contains, as at least a portion of the antimicrobial component, an active anti-viral agent (e.g., Nonoxydil-9, acyclovir, idoxuridine, and trifluridine) or a bacteriocide or bacteriostat (e.g., trichlosan, benzalkonium chloride, or the other antimicrobial agents listed in Table 2, but not limited to these agents) will control or prevent infection or serious contamination of gloved hands with viruses or bacteria, respectively, should glove integrity be compromised while handling such microbes, thereby increasing the safety of wearers. Such handcare composition may also be formulated to contain one or more antiperspirant agents (such as those described supra and listed in Table 1) in order to control moisture levels of the hands, and thereby provide additional protection against contamination by creating an environment that is less conducive to survival or growth of pathogens.

Example 4

Athletic Use

Athletic activities often subject participants to many of the same conditions that foster undesirable dermatologic effects in frequent wearers of close-fitting, non-porous protective gloves. Specifically, increased levels of perspiration, combined with close-fitting clothing and athletic hardware (e.g., gloves, running shoes, ski boots, racket handles, helmets, etc.), can lead to chronic irritation or infection of hands, feet, groin, head, and other areas of skin inside or in contact with such hardware. Such irritation or infection may arise from proliferation of natural skin flora or from contamination with pathogens present in or on moist materials, such as locker room floors, towels, and exercise equipment.

Topical application of a combined antiperspirant and antimicrobial composition of the present invention prevents or ameliorates the proliferation of such flora, thereby preventing or reducing chronic irritation or infection of the hands, feet, groin, head, and other areas of skin associated with athletic participation. Such composition may be used periodically on the skin, as needed, to control outbreaks of such flora. Moreover, such composition may be used regularly by asymptomatic individuals, for example, to reduce excessive perspiration of hands during athletic participation that might negatively affect performance.

Example 5

Cosmetic Foundation

Perspiration and excessive sebum production can cause loss of makeup from the face and other skin, and may also exacerbate formation of blemishes, such as acne, often associated with makeup use. The use of a composition (e.g., a lotion or other cosmetic foundation) containing antiperspirant and antimicrobial components according to the present invention can facilitate application of makeup and reduce makeup loss and exacerbated formation of blemishes caused by perspiration and excess sebum production when wearing such makeup.

Example 6

Foot Odor

The confinement of feet in shoes frequently leads to undesirable perspiration and odor. The use of the composition (e.g., as spray, lotion, powder, or other form) containing antiperspirant and antimicrobial components of the present invention can reduce perspiration of feet and associated foot odor.

These examples and applications are provided for illustrative purposes, as the present invention is not limited to the recited examples and applications and includes other modalities and formulations known to those skilled in the art. For example, combinations of any of the above modalities of the present invention can be combined with or in, for example, cosmetics, sun screens, after-use preparations for amelioration of symptoms of prolonged glove use or wearing of athletic equipment, or any combination of such modalities, are within the scope of the presently described invention, wherein such modalities may be used to augment the efficacy or applicability of the present invention or wherein the present invention may be used to augment the efficacy or applicability of such modalities.

Further, any combined antiperspirant and antimicrobial composition of the present invention may comprise, for example, a cream, gel, hydrogel, liquid, liquid spray, liquid suspension, lotion, ointment, aerosol spray, powder, aerosol powder, or similar formulation. For use in gloves, shoes, athletic equipment, and similar items, the composition may be applied to the relevant skin areas prior to donning such items, or may be applied to such items prior to their donning. Such composition may be added to such items at the time of manufacture (for example, inside protective gloves during manufacture). In some instances (such as on the hands), it is preferable that the composition comprise a clear liquid that does not contain moisturizing components, so as to avoid loss of dexterity or grip.

In addition to antiperspirant (such as, for example, aluminum glycinate, aluminum chlorohydrate glycinate, or zinc chlorohydrate), the composition of the present invention may also include at least one moisture sealant or humectant (such as, for example, glycerine, glycocer, glycosphingolipid, mineral oil, petrolatum, polyethylene glycol and propylene glycol) to seal moisture into the skin.

Likewise, the composition of the present invention may also include agents that suppress the host's inflammatory response (e.g., hydrocortisone or other steroidal agents or other anti-inflammatory agents, such as alclometasone dipropionate, amcinonide, betamethasone valerate, betamethasone dipropionate, clobetasone propionate, desonide, desoximetasone, diflorasone diacetate, fluocinolone acetonide, fluocinonide, flurandrenolide, fluticasone propionate, halcinonide, mometasone furoate, and triamcincolone acetonide) to enhance efficacy against irritation.

Moreover, one or more of the active ingredients may be encapsulated into a time-release vehicle (eg., liposome or similar vehicle) to enhance longevity of efficacy.

Furthermore, as a protective agent in some glove use applications, it may be preferable that the composition contain an anti-viral agent without a further antiperspirant or antibacterial component.

This description has been offered for illustrative purposes only and is not intended to limit the invention of this application.

What is claims as new and desired to be protected by Letters Patent is set forth in the appended claims.

We claim:

1. Cosmetic and medicinal compositions adapted for applying an acne-inhibiting agent to the face comprising in a cosmetic foundations;
   an antiperspirant agent and an antimicrobial agent,
   wherein said antimicrobial agent is present at a concentration of from greater than zero to approximately 0.2%, and
   wherein said antimicrobial agent is selected from the group consisting of alkydimethylbenzalkonium chloride, benzalkonium chloride, benzethonium chloride, benzyl alcohol, butylparaben, chlorhexidine, chlorobutanol, chloroxylenol, chloflucarban, cloquinol, cocamidopropyl PG-dimonium chloride phosphate, ethyl alcohol, farnesol, fluorosalan, hexachlorophene, hexylresorcinol, imidurea, iodine complex, isopropyl alcohol, mercufenol chloride, methylbenzethonium chloride, methylparaben, metronidazole, nonylphenoxypoly (ethyleneoxy) ethanoliodine, octoxy glycerine, phenol, poloxamer-iodine complex, polyhexamethylene buguanide (PHMB), propylparaben, providone iondine, quaternary ammonium compounds (QACs), secondary amyltricresols, sodium benzoate, sodium oxychlorosene, tribromsalan, triclocarban, triclosan, undecoylium chloride iodine complex, usnic acid and zinc phenosulfonate.

2. The compositions of claim 1 wherein said antiperspirant agent is selected from the group consisting of aluminum chlorohydrate, 'activated' aluminum chlorohydrate (AACH), aluminum chlorohydrate glycine complex, aluminum dichlorohydrate, aluminum sesquichlorohydrate, aluminum zirconium trichlorohydrate, aluminum zirconium tetrachlorohydrate, aluminum zirconium pentachlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, sodium aluminum chlorhydroxy lactate, aluminum zirconium tetrachlorohydrate, aluminum chlorohydrex PG complex, aluminum dichlorohydrex PG complex, aluminum sesquichlorohydrex PG complex, aluminum chlorohydrex PEG complex, aluminum dichlorohydrex PEG complex, aluminum sesquichlorohydrex PEG complex, 'activated' aluminum zirconium tetrachlorohydrex gly (AZAG), aluminum glycinate, zinc chlorohydrate, aluminum chloride, and aluminum sulfate.

3. The compositions of claim 1 further comprising an antiviral agent.

4. The compositions of claim 3 wherein said antiviral agent is selected from the group consisting of Nonoxydil-9, acyclovir, idoxuridine, and trifluridine.

5. The compositions of claim 1 further comprising a moisture sealant.

6. The compositions of claim 5 wherein said moisture sealant is selected from the group consisting of glycerine, glycocer, glycosphingolipid, mineral oil, petrolatum, polyethylene glycol and propylene glycol.

7. The compositions of claim 1 further comprising an anti-inflammatory agent.

8. The compositions of claim 7 wherein said anti-inflammatory agent is selected from the group consisting of alclometasone dipropionate, amcinonide, betamethasone valerate, betamethasone dipropionate, clobetasone propionate, desonide, desoximetasone, diflorasone diacetate, fluocinolone acetonide, fluocinonide, flurandrenolide, fluticasone propionate, halcinonide, hydrocortisone, mometasone furoate, and triamcincolone acetonide.

9. The compositions of claim 1 wherein at least one agent is encapsulated in a time-release vehicle.

10. The compositions of claim 1, wherein said compositions are applied prior to application of make-up.

11. Topical cosmetic and medicinal compositions adapted for applying an acne-inhibiting agent to the face comprising:
an antiperspirant agent and an antimicrobial agent,
wherein said antimicrobial agent is present at a concentration of from greater than zero to approximately 0.2%, and
wherein said antimicrobial agent is selected from the group consisting of alkydimethylbenzalkonium chloride, benzalkonium chloride, benzethonium chloride, benzyl alcohol, butylparaben, chlorhexidine, chlorobutanol, chloroxylenol, chloflucarban, cloquinol, cocamidopropyl PG-dimonium chloride phosphate, ethyl alcohol, farnesol, fluorosalan, hexachlorophene, hexylresorcinol, imidurea, iodine complex, isopropyl alcohol, mercufenol chloride, methylbenzethonium chloride, methylparaben, metronidazole, nonylphenoxypoly (ethyleneoxy) ethanoliodine, octoxy glycerine, phenol, poloxamer-iodine complex, polyhexamethylene buguanide (PHMB), propylparaben, providone iondine, quaternary ammonium compounds (QACs), secondary amyltricresols, sodium benzoate, sodium oxychlorosene, tribromsalan, triclocarban, triclosan, undecoylium chloride iodine complex, usnic acid and zinc phenosulfonate.

12. The cosmetic and medicinal compositions of claim 11 further comprising an antiviral agent.

13. The cosmetic and medicinal compositions of claim 11 further comprising an additional agent selected from the group consisting of a bacteriocidal agent and a bacteriostatic agent.

14. The cosmetic and medicinal compositions of claim 11 further comprising a moisture sealant.

15. The cosmetic and medicinal compositions of claim 11 further comprising an anti-inflammatory agent.

16. The cosmetic and medicinal compositions of claim 11 wherein said compositions are formulated in a delivery vehicle selected from the group consisting of liquids, semi-solids, solids and aerosols.

17. The cosmetic and medicinal compositions of claim 16 wherein said delivery vehicle is selected from the group consisting of creams, gels, hydrogels, liquids, and liquid suspensions.

18. The cosmetic and medicinal compositions of claim 11 wherein at least one agent is encapsulated in a time-release vehicle.

19. The cosmetic and medicinal compositions of claim 11, wherein said compositions are applied prior to application of make-up.

20. A pharmaceutical composition in a vehicle adapted suitable for topical administration to the face comprising:
an antiperspirant agent and an antimicrobial agent for treatment of acne,
wherein said antimicrobial agent is present at a concentration of from greater than zero to approximately 0.2%, and
wherein said antimicrobial agent is selected from the group consisting of alkydimethylbenzalkonium chloride, benzalkonium chloride, benzethonium chloride, benzyl alcohol, butylparaben, chlorhexidine, chlorobutanol, chloroxylenol, chloflucarban, cloquinol, cocamidopropyl PG-dimonium chloride phosphate, ethyl alcohol, farnesol, fluorosalan, hexachlorophene, hexylresorcinol, imidurea, iodine complex, isopropyl alcohol, mercufenol chloride, methylbenzethonium chloride, methylparaben, metronidazole, nonylphenoxypoly (ethyleneoxy) ethanoliodine, octoxy glycerine, phenol, poloxamer-iodine complex, polyhexamethylene buguanide (PHMB), propylparaben, providone iondine, quaternary ammonium compounds (OACs), secondary amyltricresols, sodium benzoate, sodium oxychlorosene, tribromsalan, triclocarban, triclosan, undecoylium chloride iodine complex, usnic acid and zinc phenosulfonate.

21. The pharmaceutical composition of claim 20 wherein said antiperspirant agent is selected from the group consisting of aluminum chlorohydrate, 'activated' aluminum chlorohydrate (AACH), aluminum chlorohydrate glycine complex, aluminum dichlorohydrate, aluminum sesquichlorohydrate, aluminum zirconium trichlorohydrate, aluminum zirconium tetrachlorohydrate, aluminum zirconium pentachlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, sodium aluminum chlorhydroxy lactate, aluminum zirconium tetrachlorohydrate, aluminum chlorohydrex PG complex, aluminum dichlorohydrex PG complex, aluminum sesquichlorohydrex PG complex, aluminum chlorohydrex PEG complex, aluminum dichlorohydrex PEG complex, aluminum sesquichlorohydrex PEG complex, 'activated' aluminum zirconium tetrachlorohydrex (AZAG), aluminum glycinate, zinc chlorohydrate, aluminum chloride, and aluminum sulfate.

22. The pharmaceutical composition of claim 20 further comprising an antiviral agent.

23. The pharmaceutical composition of claim 22 wherein said antiviral agent is selected from the group consisting of Nonoxydil-9, acyclovir, idoxuridine, and trifluridine.

24. The pharmaceutical composition of claim 20 further comprising an anti-inflammatory agent.

25. The pharmaceutical composition of claim 24 wherein said ant-inflammatory agent is selected from the group consisting of alclometasone dipropionate, amcinonide, betamethasone valerate, betamethasone dipropionate, clobetasone propionate, desonide, desoximetasone, diflorasone diacetate, fluocinolone acetonide, fluocinonide, flurandrenolide, fluticasone propionate, halcinonide, hydrocortisone, mometasone furoate, and triamcincolone acetonide.

26. A pharmaceutical composition for topical administration comprising in a cosmetic foundation:
    an antiperspirant agent and an antimicrobial agent for controlling the growth of bacteria associated with acne,
    wherein said antimicrobial agent is present at a concentration of from greater than zero to approximately 0.2% and
    wherein said antimicrobial agent is selected from the group consisting of alkydimethylbenzalkonium chloride, benzalkonium chloride, benzethonium chloride, benzyl alcohol, butylparaben, chlorhexidine, chlorobutanol, chloroxylenol, chloflucarban, cloquinol, cocamidopropyl PG-dimonium chloride phosphate, ethyl alcohol, farnesol, fluorosalan, hexachlorophene, hexylresorcinol, imidurea, iodine complex, isopropyl alcohol, mercufenol chloride, methylbenzethonium chloride, methylparaben, metronidazole, nonylphenoxypoly (ethyleneoxy) ethanoliodine, octoxy glycerine, phenol, poloxamer-iodine complex, polyhexamethylene buguanide (PHMB), propylparaben, providone iondine, quaternary ammonium compounds (QACs), secondary amyltricresols, sodium benzoate, sodium oxychlorosene, tribromsalan, triclocarban, triclosan, undecoylium chloride iodine complex, usnic acid and zinc phenosulfonate.

27. A method of reducing acne, excess sebum production and irritation caused by undesirable proliferation of dermatophytes comprising:
    applying a topical composition consisting of an antiperspirant agent and an antimicrobial agent to the skin of the face or body,
    wherein said antimicrobial agent is selected from the group consisting of alkydimethylbenzalkonium chloride, benzalkonium chloride, benzethonium chloride, benzyl alcohol, butylparaben, chlorhexidine, chlorobutanol, chloroxylenol, chloflucarban, cloquinol, cocamidopropyl PG-dimonium chloride phosphate, ethyl alcohol, farnesol, fluorosalan, hexachlorophene, hexylresorcinol, imidurea, iodine complex, isopropyl alcohol, mercufenol chloride, methylbenzethonium chloride, methylparaben, metronidazole, nonylphenoxypoly (ethyleneoxy) ethanoliodine, octoxy glycerine, phenol, poloxamer-iodine complex, polyhexamethylene buguanide (PHMB), propylparaben, providone iondine, quaternary ammonium compounds (QACs), secondary amyltricresols, sodium benzoate, sodium oxychlorosene, tribromsalan, triclocarban, triclosan, undecoylium chloride iodine complex, usnic acid and zinc phenosulfonate.

* * * * *